United States Patent [19]

Shuto et al.

[11] Patent Number: 5,200,515

[45] Date of Patent: Apr. 6, 1993

[54] 5'-TRIFLUOROMETHYL-2'-DEOXY-URIDINE PHOSPHOLIPID COMPOUNDS

[75] Inventors: Satoshi Shuto; Hiromichi Itoh; Takumi Obara; Tatsuro Fujiwara, all of Shizuoka, Japan

[73] Assignee: Asahi Kasei Kogyo Kabushiki Kaisha, Osaka, Japan

[21] Appl. No.: 701,125

[22] Filed: May 16, 1991

[30] Foreign Application Priority Data

May 16, 1990 [JP] Japan .................................. 2-126278

[51] Int. Cl.$^5$ ............................................ C07H 19/20
[52] U.S. Cl. ..................................................... 536/26.8
[58] Field of Search ......................... 536/23, 29, 28, 27

[56] References Cited

U.S. PATENT DOCUMENTS 4,797,479  1/1989  Shuto et al. ............................ 536/29

FOREIGN PATENT DOCUMENTS 86-158814  10/1984  Japan .

OTHER PUBLICATIONS

Beres et al., "Synthesis and Antitumor and Antiviral Properties of 5-Halo- and 5-(Trifluoromethyl)-2'-Deoxyuridine 3',5'-Cyclic Monophosphates and Neutral Triesters", J. Med. Chem., vol. 29, No. 7, pp. 1243-1249, Jul. 1986.

Primary Examiner—Johnnie R. Brown
Assistant Examiner—James O. Wilson
Attorney, Agent, or Firm—Young & Thompson

[57] ABSTRACT

Compounds of the formula

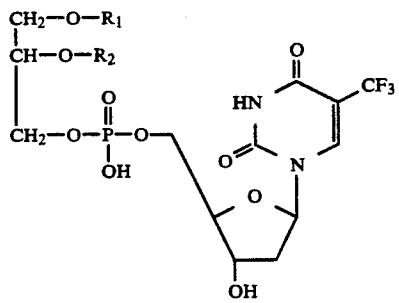

wherein $R_1$ and $R_2$ are each $C_{16-18}$ long-chain aliphatic acyl and are the same or different; and pharmacologically acceptable salts thereof are disclosed. These novel compounds are effective against 5-FU-resistant tumor cells, have low toxicity, and are not inactivated by nucleoside phosphorylase in vivo.

9 Claims, No Drawings

5′-TRIFLUOROMETHYL-2′-DEOXY-URIDINE PHOSPHOLIPID COMPOUNDS

FIELD OF THE INVENTION

The present invention relates to novel nucleoside-phospholipid conjugates and pharmacologically acceptable salts thereof. More particularly, the present invention relates to nucleoside-phospholipid conjugates of the formula [I]

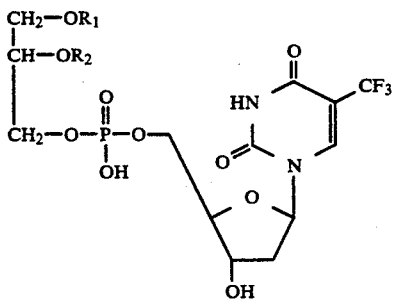

wherein $R_1$ and $R_2$ are each long-chain aliphatic acyl and are the same or different; and pharmacologically acceptable salts thereof.

BACKGROUND OF THE INVENTION

Nucleoside antitumor agents have been widely used as effective chemotherapeutics for neoplastic cells. In their application as antitumor-chemotherapeutics, however, several problems have arisen. For example, in vivo enzymatic phosphorylation of the hydroxyl group at the 5′-position of the nucleoside anti-neoplastic agent is essential to activate its antitumor activity. In addition, the agent is decomposed to an inactive substance by enzymatic reactions such as phosphorolysis or deamination. Still further, the resistance of tumor cells to antitumor agents is known to progressively increase. Lastly, the agent is in sometimes toxic to normal mitotic cells. Many different nucleoside derivatives have been synthesized in an attempt to overcome the disadvantages of known nucleoside antitumor agents.

For example, a phospholipid conjugate, 5-fluoro-2′-deoxyuridine-5′-phosphate derivative (Japan Unexam. Patent Publ. No. 61-91195) has been reported. Certain of the inventors have found that phospholipase D effectively catalyzes the transfer reaction of the phosphatidyl residue from glycerophospholipid to the primary hydroxyl group of a nucleoside, and hence a variety of nucleoside-phospholipid conjugates including arabinoside nucleoside-phospholipid conjugates can readily be prepared (U.S. Pat. No. 4,797,479).

The resistance of tumor cells to 5-fluorouracil (5-FU), a commonly used antitumor agent, is known. 2′-deoxy-5-trifluoromethyluridine is also known, which is effective against 5-FU-resistant cells and has antitumor and antiviral activities in vivo (Heiderberger et al., Cancer Res., Vol. 24, p. 1979 (1964), H. E. Kaufman et al., Science, Vol. 145, p. 585 (1964)). 2′-deoxy-5-trifluoromethyluridine is, however, decomposed by the action of thymidine phosphorylase in vivo, and is not effective for clinical use. Hence, 2′-deoxy-5-trifluorouridine derivatives which are effective against 5-FU-resistant tumor cells but which are not inactivated by nucleoside phosphorylase in vivo, are desired.

SUMMARY OF THE INVENTION

We have found that novel nucleoside-phospholipid conjugates of the formula [I], and pharmacologically acceptable salts thereof, show activities against 5-FU-resistant tumor cells and are not decomposed by nucleoside phosphorylase in vivo.

An object of the present invention is to provide novel nucleoside-phospholipid conjugates of the formula [I]

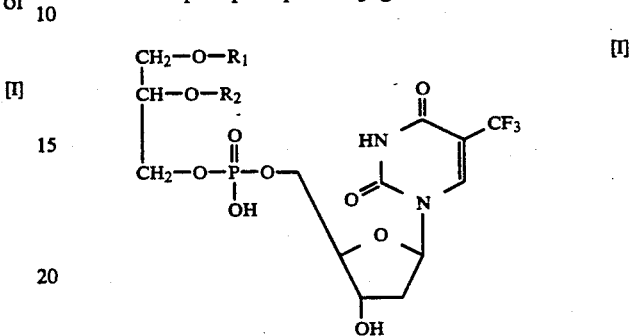

wherein $R_1$ and $R_2$ have the same meanings as before, as well as pharmacologically acceptable salts thereof.

DETAILED DISCUSSION

Examples of glycerophospholipids suitable for preparing the nucleoside-phospholipid conjugates of the formula [I] are phosphatidylcholines of the formula [II]

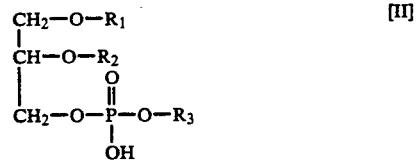

wherein $R_1$ and $R_2$ have the same meanings as before, and $OR_3$ is a choline residual.

In the phosphatidylcholine series of glycerophospholipid, $R_1$ and $R_2$ are the same or different and are long chain aliphatic acyl. Preferably, the group $R_1$ is $C_{16-18}$ saturated or unsaturated long chain aliphatic acyl and $R_2$ is the same or a different $C_{16-18}$ saturated or unsaturated long chain aliphatic acyl. For example, $R_1$ can be long chain saturated or unsaturated aliphatic acyl such as palmitoyl, stearoyl or oleoyl, and $R_2$ can be saturated or unsaturated long chain aliphatic acyl such as palmitoyl, stearoyl, oleoyl or linoleoyl. Preferred examples are dipalmitoyl phosphatidylcholine wherein $R_1$ and $R_2$ are both palmitoyl; dioleoyl phosphatidylcholine wherein $R_1$ and $R_2$ are both oleoyl; distearoyl phosphatidylcholine wherein $R_1$ and $R_2$ are both stearoyl; and a phosphatidylcholine compound wherein $R_1$ is palmitoyl or stearoyl and $R_2$ is oleoyl or linoleoyl. These phosphatidyl cholines can be synthesized according to known organic synthesis techniques, although at least some of them are also commercially available.

An example of the nucleoside to be incorporated into the compounds of the invention is 2′-deoxy-5-trifluoromethyluridine.

Nucleoside-phospholipid conjugates of the formula [I] can be obtained by reacting a glycerophospholipid derivative as described above with nucleoside, in the presence of phospholipase D and if required metallic ion, and in a suitable solvent. A preferred example of phospholipase D is phospholipase D-P (hereinafter sometimes designated PLDP) obtained by culturing a broth of Streptomyces sp. AA586 FERM P-6100 (Japanese Patent Unexam. Publ. No. 58-152481, Toyo Jozo Co., Catalog No. P-39). The amount of enzyme is at least 0.1 unit phospholipase D-P per 1 mg of phosphatidyl choline, and is preferably 1-100 units.

Examples of suitable solvents include two-phase systems of organic solvent and aqueous solvent, for example mixtures of an organic solvent such as ether, benzene, methylenechloride, ethyl acetate or chloroform and a buffer solution of pH 3-10, preferably pH 3-6.

A general example of a water soluble salt for generation of metallic ion is calcium chloride.

The reaction temperature is generally 10°-60° C. and the reaction time is 30 mins. to 5 days. The preferred conditions are: reaction at 25°-45° C. for 30 mins.-2 days, using 500-10,000 units PLDP and 0.1-5 m mol of phosphatidyl choline per 1 m mol of 2'-deoxy-5-trifluoromethyluridine, in a two-phase solvent system of aqueous solvent at pH 4-7 and chloroform or benzene. The thus-obtained nucleoside-phospholipid conjugates according to the invention can be purified by a partition method and silica-gel chromatography.

The one-step synthesis of nucleoside-phospholipid conjugates according to the present invention is illustrated as follows:

antineoplastic nucleoside 5'-monophosphate of 2'-deoxy-5-trifluoromethyluridine is generated in cells without the action of kinase; and their longer action and increased activity are accompanied by a low toxicity.

The novel nucleoside-phospholipid conjugates of the present invention reveal marked antitumor activity in vivo as well as cytotoxic activity against 5-FU-resistant cells.

Antitumor activity against Meth A fibrosarcoma cells and 5-FU-resistant P 388 leukemia cells are shown in the ensuing examples, according to the following list of specifications:

Animals:
BALB/c mice, male, age 6 weeks;
$BDF_1$ mice, male, age 5 weeks;
Charles River Japan Inc., five mice in an experimental group and seven mice in a control group.

Tumor cells:
Meth A fibrosarcoma cells: $1 \times 10^6$ cells/0.2 ml are inoculated subcutaneously in the abdomen of BALB/c mice.

5-FU-resistant P 388 leukemia cells: 5-FU-resistant P 388 leukemia cells are established by intraperitoneally administering 20 mg/kg of 5-FU, once a day, in P 388 leukemia cell-intraperitoneally inoculated $BDF_1$ mice, and spawning seven successive generations. The said resistant cells show a 50-fold resistance to 5-FU. $1 \times 10^6$ cells/0.2 ml are inoculated intraperitoneally in $BDF_1$

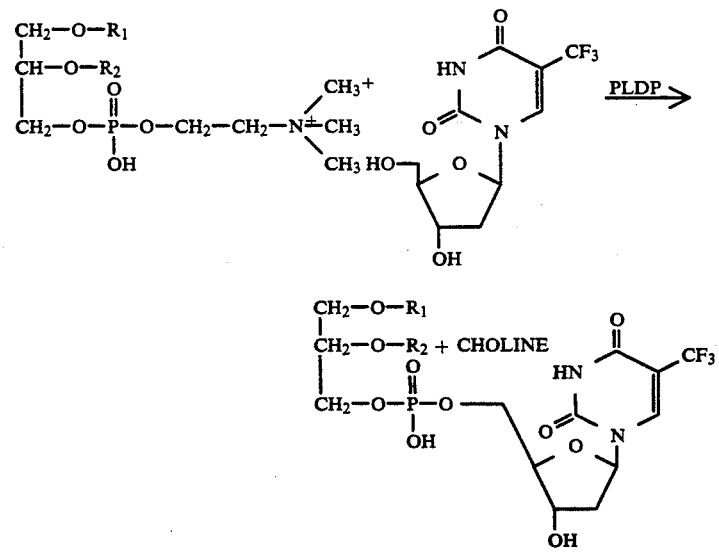

The thus-obtained nucleoside-phospholipid conjugate is a novel compound wherein the phosphate group of the phospholipid and the primary hydroxy group at the 5'-position of 2'-deoxy-5-trifluoromethyluridine are bonded.

The thus-obtained product can be prepared as a non-toxic, pharmacologically acceptable salt, such as a sodium salt, and can be administered in general orally or in the form of a suspension in sterilized distilled water.

The thus-prepared nucleoside-phospholipid-conjugates of the present invention have the advantages that: they are more lipophilic as compared with the original nucleoside, 2'-deoxy-5-trifluoromethyluridine; they are not easily excreted, that is, they are more active for a longer time; they are not affected by enzymatic inactivation reactions such as phosphorolysis by phosphorylase; they have higher affinity to cell membranes; the mice.
Samples:

| Compound No. | $R_1$ | $R_2$ | Nucleoside Residue |
|---|---|---|---|
| 1 | palmitoyl | palmitoyl | $TF_3Udr$ |
| 2 | stearoyl | stearoyl | $TF_3Udr$ |
| 3 | oleoyl | oleoyl | $TF_3Udr$ |
| 4 | palmitoyl | oleoyl | $TF_3Udr$ |
| 5 | palmitoyl | linoleoyl | $TF_3Udr$ |
| 6 | stearoyl | oleoyl | $TF_3Udr$ |
| 7 | stearoyl | linoleoyl | $TF_3Udr$ |
| 8 | palmitoyl | palmitoyl | FUDR |

$TF_3Udr$: 2'-deoxy-5-trifluoromethyluridine-5'-yl
FUDR: 2'-deoxy-5-fluorouridine-5'-yl.

Preparation of samples and administration of drugs:

Samples are suspended or dissolved in distilled water up to the desired concentration by sonication. 0.1 ml/10 g body weight is administered.

Administration: starting 24 hours after inoculation of tumor cells, once a day for five days orally or intraperitoneally.

Evaluation of the effect:

In Meth A fibrosarcoma-inoculated mice, the tumor volume is determined by measuring the minor axis and major axis of the tumor and calculating according to the following equation:

volume of tumor $(mm^3)=[minor\ axis(mm)]^2 \times major\ axis(mm)/2$.

Evaluation is determined by the value T/C (%) according to the average tumor volume (C) of the control group and the average tumor volume (T) of the treated group.

In the 5-FU-resistant P 388 leukemia transplanted group, an evaluation is made according to an increase in life span with respect to the control group (ILS %).

Results: Referring to an evaluation standard for antitumor effect established by the U.S. National Cancer Institute (NCI), a significant antitumor effect on 5-FU-resistant P 388 leukemia is said to occur for a value ILS 25% or higher and on Meth A fibrosarcoma for a value T/C below 40%.

As shown in Table 1, each of the nucleoside-phospholipid conjugates of the present invention (compounds 1–7) illustrated in this Table is administered at 0.1 m mol/kg/day for five successive days, and each is shown to suppress growth of Meth A fibrosarcoma to a value significantly below T/C 40%. In contrast, the parent compound 2'-deoxy-5-trifluoromethyluridine shows Meth A fibrosarcoma growth inhibition at a value of T/C 61.2% which reveals no significant antitumor effect. A temporary slight decrease in body weight is observed for a single 0.5 m mol/kg oral administration, however no death in any experimental group is observed.

Also, as shown in Table 2, the compounds of the present invention show significant antitumor activity against 5-FU-resistant P 388 leukemia, with a value of ILS 40–45%. However, the phospholipid conjugate of 2'-deoxy-5-fluorouridine wherein the side chain is long chain acyl (compound 8), as described in Japanese Patent Unexam. Publ. No. 61-91195, is shown obviously to have no antitumor activity against 5-FU-resistant P 388 leukemia.

TABLE 1

| Antitumor Effect Against Meth A Fibrosarcoma (sc-po) | | | |
|---|---|---|---|
| Compound No. | Dose (m mol/kg/day) | Total Dose (m mol/kg/mice) | T/C (%) 14th Day |
| 1 | 0.1 | 0.5 | 23.8** |
| 2 | 0.1 | 0.5 | 37.3* |
| 3 | 0.1 | 0.5 | 32.1** |
| 4 | 0.1 | 0.5 | 29.8** |
| 5 | 0.1 | 0.5 | 22.2** |
| 6 | 0.1 | 0.5 | 36.3* |
| 7 | 0.1 | 0.5 | 26.6** |
| A parent compound (2'-deoxy-5-trifluoromethyluridine) | 0.1 | 0.5 | 61.2 |

N = 5
**p <0.01
*p <0.05
Significant difference is checked by Student's t-test.

TABLE 2

| Antitumor Effect Against 5-FU-Resistant P 388 Leukemia (ip-ip) | | | |
|---|---|---|---|
| Compound No. | Dose (m mol/kg/day) | Total Dose (m mol/kg/mice) | ILS (%) |
| 1 | 0.03 | 0.15 | 45.0 |
| 5 | 0.03 | 0.15 | 40.0 |
| 8 | 0.01 | 0.05 | 11.0 |
| 8 | 0.03 | 0.15 | −14.0 |
| 5-FU | 0.15 | 0.75 | 8.0 |

The following examples illustrate the present invention but are not to be construed as limiting.

EXAMPLE 1

2'-Deoxy-5-trifluoromethyluridine (237 mg, 0.8 mM) was dissolved in 0.2M acetate buffer (pH 5.7, 20 ml) containing 0.25M CaCl$_2$ (2 ml). PLDP (phospholipase D-P produced by microorganisms of the genus Streptomyces, Toyo Jozo Co., specific activity 160 units/mg, 30 mg) and a solution of 1,2-dipalmitoyl-sn-glycero-3-phosphocholine (1.76 g) in chloroform (60 ml) were added thereto, and the resultant mixture was then stirred at 45° C. for 6 hours. To the reaction mixture were added methanol (30 ml) and water (13 ml), and the resultant mixture was then partitioned. The organic layer was dried in vacuo. The residue was purified by means of a silica-gel flash column (Merck Art 9385 silica-gel) (solvent system; chloroform→chloroform:methanol=20:1→ditto 10:1→ditto 4:1).

The eluate fraction containing the product was dried in vacuo and the resultant residue was dissolve din a mixture of chloroform and methanol (2:1) (40 ml) and separated by adding 0.5 N HCl. The organic layer was washed twice with water, then dried in vacuo. The residue was dissolved in a mixture of chloroform:methanol:water (10:5:1) (40 ml), with the resulting solution being charged on a column of Diaion WK-20 resin (Na type, Mitsubishi Chem. Co.) and eluted with the same solvent mixture. The eluate was recovered and dried to obtain a sodium salt of the product.

Yield: 477 mg.
UV methanol $\lambda^{max}=261$ nm.
MS (FAB) m/e=949 (MNa$^+$).

EXAMPLES 2–7

In Example 1, the compound 1,2-dipalmitoyl-sn-glycero-3-phosphocholine was replaced by a series of glycerophospholipids of the formula [I] wherein R$_1$ and R$_2$ are as illustrated in Table 3, to obtain the products 2–7 in Table 3.

TABLE 3

| Compound No | R$_1$ | R$_2$ | yield | UV methanol $\lambda$max | MS (FAB) |
|---|---|---|---|---|---|
| ② | stearoyl | stearoyl | 396 mg | 261 nm | m/e 1005 (MNa$^+$) |
| ③ | oleoyl | oleoyl | 398 mg | 261 nm | m/e 1001 (MNa$^+$) |

TABLE 3-continued

| Compound No | $R_1$ | $R_2$ | yield | UV methanol $\lambda$max | MS (FAB) |
|---|---|---|---|---|---|
| ④ | palmitoyl | oleoyl | 401 mg | 261 nm | m/e 975 (MNa+) |
| ⑤ | palmitoyl | linoleoyl | 293 mg | 261 nm | m/e 973 (MNa+) |
| ⑥ | stearoyl | oleoyl | 421 mg | 261 nm | m/e 1003 (MNa+) |
| ⑦ | stearoyl | linoleoyl | 286 mg | 261 nm | m/e 1001 (MNa+) |

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

What is claimed is:

1. Compounds of the formula

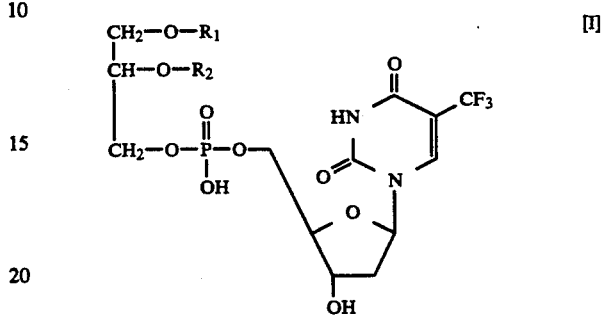

wherein $R_1$ and $R_2$ are each $C_{16-18}$ long-chain aliphatic acyl and are the same or different; and pharmacologically acceptable salts thereof.

2. The compounds according to claim 1, wherein $R_1$ is selected from the group consisting of palmitoyl, stearoyl and oleoyl, and $R_2$ is selected from the group consisting of palmitoyl, stearoyl, oleoyl and linoleoyl.

3. A compound according to claim 2, wherein $R_1$ and $R_2$ are stearoyl.

4. A compound according to claim 2, wherein $R_1$ and $R_2$ are oleoyl.

5. A compound according to claim 2, wherein $R_1$ and $R_2$ are palmitoyl.

6. A compound according to claim 2, wherein $R_1$ is palmitoyl and $R_2$ is oleoyl.

7. A compound according to claim 2, wherein $R_1$ is palmitoyl and $R_2$ is linoleoyl.

8. A compound according to claim 2, wherein $R_1$ is stearoyl and $R_2$ is oleoyl.

9. A compound according to claim 2, wherein $R_1$ is stearoyl and $R_2$ is linoleoyl.

* * * * *